United States Patent [19]

Kawahara

[11] Patent Number: 5,261,413
[45] Date of Patent: Nov. 16, 1993

[54] BLOOD PRESSURE MEASURE SYSTEM

[75] Inventor: Yoshimi Kawahara, Kohnan, Japan

[73] Assignee: Colin Electronics Co., Ltd., Aichi, Japan

[21] Appl. No.: 736,689

[22] Filed: Jul. 26, 1991

[30] Foreign Application Priority Data

Aug. 2, 1990 [JP] Japan .................. 2-82459[U]
Aug. 2, 1990 [JP] Japan .................. 2-82460[U]

[51] Int. Cl.$^5$ .................................. A61B 5/02
[52] U.S. Cl. .............................. 128/682; 128/683
[58] Field of Search .............. 128/683, 682, 681, 680, 128/679, 678, 677, 672

[56] References Cited

U.S. PATENT DOCUMENTS

| | | | |
|---|---|---|---|
| 3,550,582 | 12/1970 | Wilhelmson | 128/683 |
| 4,326,536 | 4/1982 | Kitagawa et al. | 128/682 |
| 4,367,751 | 1/1983 | Link et al. | 128/681 |
| 4,459,991 | 7/1984 | Hatschek | 128/682 |
| 4,475,557 | 10/1984 | Hatschek et al. | 128/681 |
| 4,660,567 | 4/1987 | Kaneko et al. | 128/682 |
| 4,796,184 | 1/1989 | Bahr et al. | 128/682 |
| 4,922,918 | 5/1990 | Ruiter | 128/681 |
| 4,969,466 | 11/1990 | Brooks | 128/681 |
| 5,094,244 | 3/1992 | Callahan et al. | 128/677 |
| 5,099,851 | 3/1992 | Hata et al. | 128/677 |

Primary Examiner—Lee S. Cohen
Assistant Examiner—Samuel Gilbert
Attorney, Agent, or Firm—Oliff & Berridge

[57] ABSTRACT

A blood pressure monitor system including a pressing device for pressing a body portion of a subject, a measuring device for increasing the pressing force of the pressing device to a predetermined level, subsequently varying the pressing force, and measuring a blood pressure of the subject during the variation of the pressing force, the measuring device repeating the blood pressure measurement, a setting device for setting a frequency at which the measuring device repeats the blood pressure measurement, and a changing device for changing a rate of increase of the pressing force depending upon the measurement frequency set by the setting device. A blood pressure measure system including a pressing device for pressing a body portion of a subject, an automatic regulating device for step-wise increasing the pressing force of the pressing device to a predetermined level, the step-wise increase of the pressing force including alternate first and second periods, the pressing force being increased in each of the first periods and maintained in each of the second periods, and a measuring device for measuring a blood pressure of the subject while the pressing force is decreased after the step-wise increase.

14 Claims, 5 Drawing Sheets

BLOOD PRESSURE MEASURE SYSTEM

BACKGROUND OF THE INVENTION

Field of the Invention

The present invention relates to a blood pressure monitor or measuring device.

Related Art Statement

There is known a blood pressure monitor system including (a) a pressing device such as a cuff for pressing a body portion of a subject, and (b) a measuring device for increasing the pressing force of the pressing device to a predetermined level, subsequently varying the pressing force, and measuring a blood pressure of the subject based on Korotkoff sounds or pulse waves obtained during the variation of the pressing force, the measuring device repeating the blood pressure measurement at a pre-set period. In the case where frequent blood pressure measurements from a patient are necessary, for example, during or after a surgical operation, the measurement period is set at a short time on the monitor system. On the other hand, for a patient under a stable condition, for example, in a general ward, the measurement period is set at a long time.

For a patient such as during or after a surgical operation, it is desirable, in addition to the use of a short measurement period, to increase the pressing force (e.g., cuff pressure) quickly so as to measure blood pressure as fast as possible in each of the periodic measurement cycles.

On the other hand, for a patient under a stable condition for whom a long measurement period is used, it is not necessary to measure blood pressure so quickly in each periodic measurement cycle. Rather, it is desirable to increase the cuff pressure slowly so as to reduce mental burden to the patient and prevent congestive spots from being produced on the patient's skin. This is very important, in particular, in the case where the blood pressure of a patient received in a general ward is monitored over a long period of time.

However, in the conventional blood pressure monitor system, the pressing force (e.g., cuff pressure) increase rate is not is varied, that is, it is kept constant for both urgent and stable cases, and therefore fails to simultaneously satisfy the above indicated requirements for the urgent and stable cases.

In addition, there is known a blood pressure measuring system including (1) a pressing device such as a cuff for pressing a body portion of a subject, and (2) a measuring device for automatically measuring a blood pressure of the subject based on Korotkoff sounds or pulse waves obtained while the pressing force is decreased after having been increased to a predetermined level. In this measuring system, the pressing force (e.g., cuff pressure) automatically is increased, for example, with pressurized air being supplied from an air pump.

However, a patient whose upper arm is subject to automatic cuff pressure increase by the above measuring system, may feel such uneasiness or pain as he or she would not feel when undergoing manual cuff pressure increase. This may badly affect the accuracy of blood pressure measurement. In addition, the conventional automatic cuff pressure increase may cause congestive spots to come out on the patient's skin.

The Applicant has recognized that the reason for a patient to feel uneasiness or pain when being subject to the conventional automatic cuff pressure increase is that the patient feels as if he or she would be pressed by the cuff endlessly because the cuff pressure is increased continuously without any pauses in contrast to the manual cuff pressure increase in which the cuff pressure is increased step-wise including pauses. Also, the Applicant has found that the reason for congestive spots to come out on patient's skin due to the conventional automatic cuff pressure increase is that wrinkles produced in the cuff surface can not be recovered to its original smooth state because of the continuous cuff pressure increase without any pauses

SUMMARY OF THE INVENTION

It is therefore a first object of the present invention to provide a blood pressure monitor system which measures blood pressure quickly in each periodic measurement cycle for an urgent case and which does not burden a patient under a stable condition or does not cause congestive spots to come out on the patient's skin.

It is a second object of the present invention to provide a blood pressure measuring system which measures blood pressure of a subject by effecting automatic pressing force increases without causing the subject to feel uneasiness or pain.

The above first object has been achieved according to a first aspect of the present invention, which provides a blood pressure monitor system comprising (a) pressing means for pressing a body portion of a subject, (b) measuring means for increasing the pressing force of the pressing means to a predetermined level, subsequently varying the pressing force, and measuring a blood pressure of the subject during the variation of the pressing force, the measuring means repeating the blood pressure measurement, (c) setting means for setting a frequency at which the measuring means repeats the blood pressure measurement, and (d) changing means for changing a rate of increase of the pressing force depending upon the measurement frequency set by the setting means.

In the blood pressure monitor system constructed as described above, the changing means changes a rate of increase of the pressing force depending upon the measurement frequency set by the setting means. More specifically, in the case where the measurement frequency is set at a great value, that is, the measurement period is set at a small value for monitoring the blood pressure of a patient, for example, during or after a surgical operation, the changing means selects a high pressing force increase rate so as to shorten the time necessary for blood pressure measurement. Consequently, a doctor or nurse can obtain a blood pressure value very quickly in each periodic measurement cycle for an urgent case. A patient who is under anesthesia during or after a surgical operation does not feel pain or mental burden even though the pressing force is increased at a high rate.

On the other hand, in the case where the measurement period is set at a long time for a patient under a stable condition, the changing means selects a low pressing force increase rate so as to relieve the patient of the mental burden or the congestive spots on the patient's skin. In addition, in the case where the low pressing force increase rate is established with an air pump being operated at a low rotational speed, noise produced from the pump is accordingly reduced, which allows the other patients in a general ward to sleep at nights without being disturbed by such noise.

According to a feature of the first aspect of the invention, the changing means judges whether or not the measurement frequency is greater than a reference value, and selects a first pressing force increase rate if the judgement is negative and a second pressing force increase rate higher than the first increase rate if the judgement is affirmative.

According to another feature of the first aspect of the invention, the pressing means comprises an inflatable cuff, the measuring means comprises an air pump which supplies the cuff with pressurized air, and the changing means comprises a pump drive/regulate circuit which changes a rotational speed of the air pump in two steps depending upon the selected first or second increase rate.

According to yet another feature of the first aspect of the invention, the setting means is manually operated to set a measurement period as the measurement frequency, the setting means generating to the changing means an electrical signal representing the measurement period.

The above second object has been achieved according to a second aspect of the present invention, which provides a blood pressure measuring system comprising (1) pressing means for pressing a body portion of a subject, (2) automatic regulating means for step-wise increasing the pressing force of the pressing means to a predetermined level, the step-wise increase of the pressing force including alternate first and second periods, the pressing force being increased in each of the first periods and maintained in each of the second periods, and (c) measuring means for measuring a blood pressure of the subject while the pressing force is decreased after the step-wise increase.

In the blood pressure measuring system constructed as described above, the automatic regulating means step-wise increases the pressing force of the pressing means to a predetermined level, such that the step-wise pressing force increase includes alternate first and second periods, the pressing force being increased in each of the first periods and maintained in each of the second periods. Thus, the present measure system is free from the problem that a subject may feel as if he or she would be pressed endlessly when undergoing automatic continuous pressing force (e.g. cuff pressure) increase, thereby relieving the subject of such uneasiness or pain as he or she might feel due to the conventional monotonous cuff pressure increase. This results in preventing the accuracy of blood pressure measurement from being deteriorated because of that uneasiness or pain. In addition, wrinkles produced by cuff pressurization are restored to their original smooth state during each of the second periods in which the pressing force is maintained. This contributes to preventing congestive spots from being produced on subject's skin.

According to a feature of the second aspect of the invention, the pressing means comprises an inflatable cuff, and the regulating means comprises an open/close valve, an air reservoir, and an air pump which supplies the reservoir with pressurized air, the open/close valve being opened during the each first period so as to allow the pressurized air stored in the reservoir to be supplied to the cuff and thereby increase a pressure in the cuff, the open/close valve being closed during the each second period so as to maintain the pressure in the cuff.

According to another feature of the second aspect of the invention, the measuring system further comprises a means for, in the each second period, increasing a pressure in the reservoir with the pressurized air from the pump, to an upper limit of a predetermined pressure range, and subsequently maintaining the reservoir pressure within the pressure range.

According to yet another feature of the second aspect of the invention, the regulating means effects the step-wise pressing force increase after having continuously increased the pressing force to a predetermined low level.

According to a further feature of the second aspect of the invention, the regulating means utilizes constant values as the first and second periods, respectively.

In a preferred embodiment according to the second aspect of the invention, the regulating means increases the pressing force by a predetermined value in the each first period.

In another embodiment according to the second aspect of the invention, the measuring means periodically measures the blood pressure at predetermined intervals of time.

BRIEF DESCRIPTION OF THE DRAWINGS

The above and optional objects, features and advantages of the present invention will be better understood by reading the following detailed description of the presently preferred embodiments of the invention when considered in conjunction with the accompanying drawings, in which.

DETAILED DESCRIPTION OF THE PREFERRED EMBODIMENTS

Figure 1:
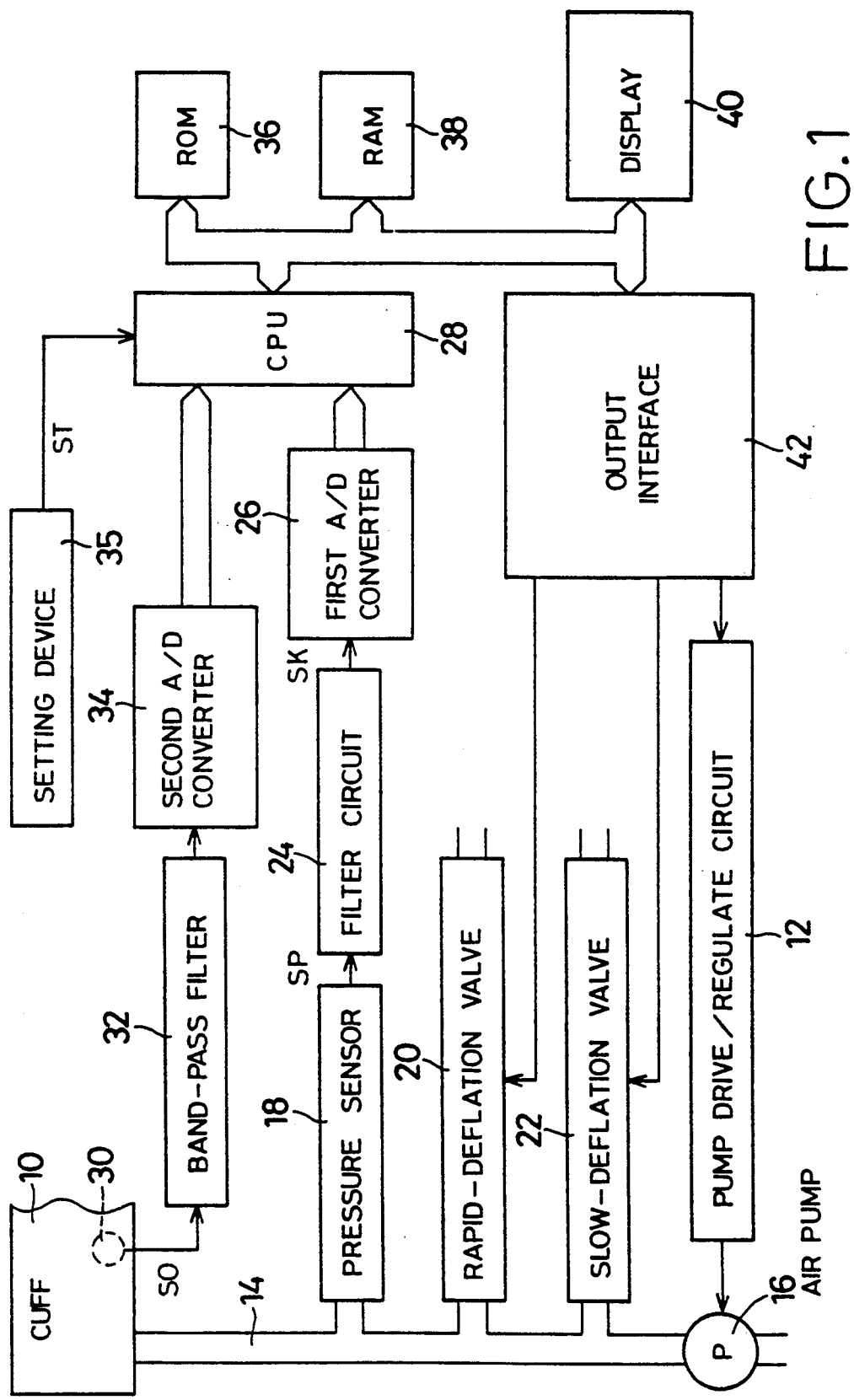
FIG. 1 is a diagrammatic view of a blood pressure monitor system embodying the present invention.

Referring first to FIG. 1, there is shown the circuit diagram of a blood pressure monitor system embodying the present invention.

In FIG. 1, reference numeral 10 designates a rubber bag or cuff adapted to be set around an upper arm or the like of a living subject. An air pump 16 is connected to the cuff 10 via piping 14. The rotational speed of the air pump 16 is regulated by a pump drive/regulate circuit 12. The pump circuit 12 is responsive to a drive signal supplied from an output interface 42 (described later), to step-wise change the rotational speed of the air pump 16, more specifically, in the present embodiment, in two steps, so that air pressure in the cuff 10 (hereinafter, referred to as the "cuff pressure") is increased at a low or a high rate by being supplied with pressurized air from the pump 16. Consequently, the upper arm of the subject is pressed by the inflated cuff 10. In the present embodiment, the cuff 10 serves as pressing means.

A pressure sensor 18, a rapid-deflation valve 20, and a slow-deflation valve 22 are associated with the piping 14 in a parallel relationship with each other. The pressure sensor 18 detects the cuff pressure and generates a pressure signal SP representing the detected cuff pressure, to a filter circuit 24. The filter circuit 24 includes a low-pass filter which transmits only a component representing a static pressure out of the cuff pressure (hereinafter, the component is referred to as the "cuff pressure signal SK"). The cuff pressure signal SK is supplied to a central processing unit (CPU) 28 via a first analog to digital (A/D) converter 26.

A microphone 30 is associated with the cuff 10. The microphone 30 detects arterial sounds (i.e., Korotkoff sounds) produced from an artery running in the upper arm of the subject, and generates a sound signal SO representing the detected Korotkoff sounds, to a bandpass filter 32. The band-pass filter 32 transmits only a component having a frequency of about 30 to 80 Hz. The sound signal SO is supplied to the CPU 28 via a second A/D converter 34.

A setting device 35 is connected to the CPU 28. Before starting a blood pressure monitoring, an operator such as a doctor or nurse manually operates the setting device 35 for setting a period (or frequency) of blood pressure measurements. The setting device 35 generates to the CPU 28 a period signal ST representing the set period.

The CPU 28 is connected via data bus to a read only memory 36, a random access memory 38, a display 40, and the output interface 42. The CPU 28 processes input signals by utilizing control programs pre-stored in the ROM 36 and temporary-storage function of the RAM 38, and generates drive signals via the output interface 42 to the pump drive/regulate circuit 2 and drive circuits (not shown) for the rapid- and slow-deflation valves 20, 22, so as to regulate the air pump 16 and the two valves 20, 22, respectively. In addition, the CPU 28 operates for determining a blood pressure of the subject by utilizing the sound signal SO and cuff pressure signal SK, and commands the display 40 to indicate the determined blood pressure.

Figure 2:
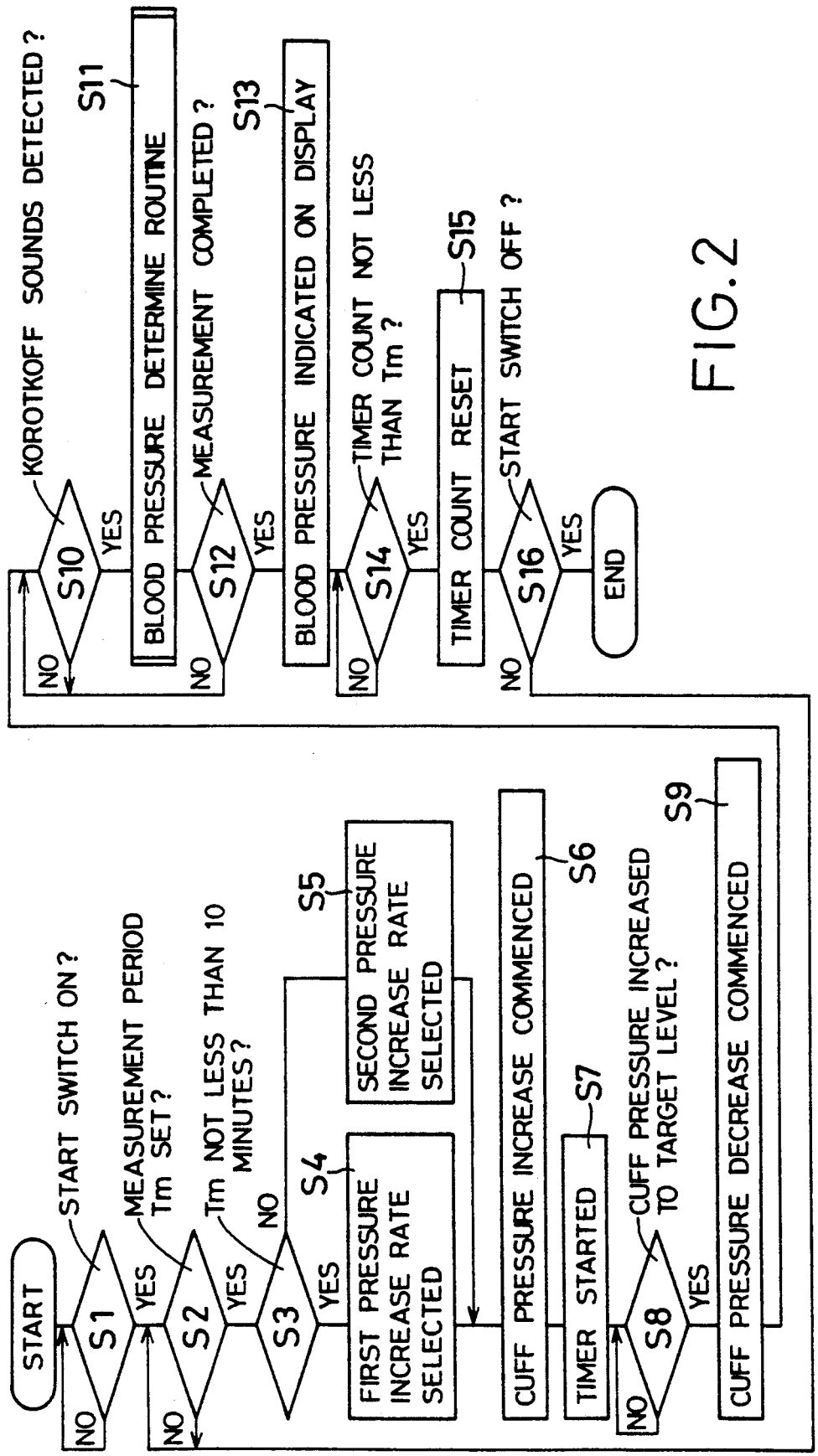
FIG. 2 is a flow chart for illustrating the operation of the monitor system of FIG. 1.

Hereinafter, there will be described the operation of the blood pressure monitor system constructed as described above, by reference to the flow chart of FIG. 2.

Upon application of electric power to the monitor system, the CPU 32 effects initialization operations, and subsequently the control of the CPU 32 proceeds with Step S1 to identify whether or not a start switch (not shown) has been turned ON. If a negative judgement is made in Step S1, the control of the CPU 32 repeats Step S1 until an affirmative judgement is made. On the other hand, if an affirmative result is provided in Step S1, the control goes to Step S2 to identify whether or not the period signal ST representing a set period, $T_m$, is present at the CPU 32. In the case where a negative result is provided in Step S2, the control repeats Step S2 and waits for an affirmative judgement. In the case where an affirmative judgement is made in Step S2, the control of the CPU 32 goes to Step S3 to judge whether or not the set period $T_m$ is not smaller than a reference value, in the present embodiment, 10 minutes. If an affirmative judgement is made in Step S3, the control goes to Step S4 to select a first pressure increase rate so that the cuff pressure is increased at a low rate, and then proceeds to Step S6. On the other hand, if a negative judgement is made in Step S3, the control goes to Step S5 to select a second pressure increase rate higher than the first pressure increase rate so that the cuff pressure is increased at a high rate, and then proceeds to Step S6.

In Step S6, both the rapid- and slow-deflation valves 20, 22 are closed, and the air pump 16 is driven or rotated by the drive/regulate circuit 12 at the low or high rate selected in Step S4 or Step S5. Thus, the cuff pressure starts to be increased. In the present embodiment, Steps S3 through S5 and the pump drive/regulate circuit 12 cooperate with each other to serve as pressure increase rate changing means.

Step S6 is followed by Step S7 in which a timer (not shown) starts to count for measuring a time lapse from the commencement of the cuff pressure increase. Subsequently, the control of the CPU 32 goes to Step S8 to identify whether or not the cuff pressure has exceeded a reference pressure level (e.g., 180 mmHg) which is estimated to be greater than the systolic blood pressure of the subject. If a negative judgement is made in Step S8, the control of the CPU 32 repeats Step S8 until an affirmative judgement is made. If the cuff pressure has exceeded the reference pressure level and an affirmative judgement is made in Step S8, the control goes to Step S9 in which the rotation of the air pump 16 is stopped and the slow-deflation valve 22 is opened. Consequently, the cuff pressure starts to be decreased slowly.

Step S9 is followed by Step S10 to identify whether or not a Korotkoff sound has been detected, by utilizing the sound signal SO. In the case where a negative judgement is made in Step S10, the control waits for an affirmative judgement. When an affirmative result is provided, a magnitude of the signal SO corresponding to the Korotkoff sound, and a magnitude of the cuff pressure signal SK at the time of detection of the Korotkoff sound, are stored in the RAM 38, in Step S10. Step S10 is followed by Step S11, namely, blood pressure determine routine.

In Step S11, a well-known blood pressure determine algorithm is implemented to determine, as systolic and diastolic blood pressures, the cuff pressures at the time of appearance and disappearance of the Korotkoff sounds, respectively. Step S11 is followed by Step S12 to identify whether or not the blood pressure measurement has been completed. If the measurement has not ended and therefore a negative judgement is made in Step S12, the control goes back to repeat Step S10 through Step S12. On the other hand, if the measurement has been completed and an affirmative judgement is made in Step S12, the control goes to Step S13 to indicate the measured blood pressures on the display 40. In addition, the rapid-deflation valve 20 is opened.

Step S13 is followed by Step S14 to judge whether or not a value, T, counted by the previously-described timer has exceeded the set period $T_m$. If a negative judgement is made in Step S14, the control of the CPU 32 repeats this step until an affirmative judgement is made. Meanwhile, if the value T has exceeded the period $T_m$ and accordingly an affirmative judgement is made in Step S14, the control goes to Step S15 to reset the timer count T to zero. Step S15 is followed by Step S16 to judge whether or not the previously-described start switch has been turned OFF. In the case where an affirmative judgement is made in Step S16, the control of the CPU 32 quits this program. On the other hand, if a negative judgement is made in Step S16, the control goes back to Steps S2 and the following steps for carrying out another blood pressure measurement. Thus, blood pressure measurements successively are carried out at the period $T_m$ (that is, at a frequency corresponding to the period $T_m$), and the measured blood pressures are indicated on the display 40 for each of the periodic measurement cycles.

As is apparent from the foregoing description, the present blood pressure monitor system operates in such a way that, in the case where the measurement period $T_m$ is set at less than 10 minutes in an urgent situation such as during or after a surgical operation, the previously-described second (high) pressure increase rate is selected, so that the cuff pressure (pressure in the cuff 10) is increased quickly. As a result, the time necessary to carry out a blood pressure measurement advantageously is shortened. In the urgent situation, therefore, blood pressure can be measured in a shorter time in each periodic measurement cycle. A patient under anesthesia during or after a surgical operation would not feel pain even if the cuff pressure is increased at the high rate. On the other hand, in the case where the measurement period $T_m$ is set at not less than 10 minutes because of low necessity of the blood pressure measurement, the present monitor system selects the second (low) pressure increase rate, so that the cuff pressure is increased slowly. In this case, the patient advantageously is prevented from pain or congestion in the upper arm due to quick pressing by the cuff 10.

In the above latter case, namely, the case where the second pressure increase rate is selected, the air pump 16 is driven at a lower rotational speed than that for the first pressure increase rate. Accordingly, noise produced from the air pump 16 is reduced, which allows other patients in a general ward, for example, to sleep without being disturbed by such noise.

While, in the present embodiment, 10 minutes is used as the reference measurement period for selecting one of the two steps, namely, first and second pressure increase rates, it is possible to employ a different reference period than 10 minutes, or to change the pressure increase rate among three or more steps.

Although, in the present embodiment, changing the pressure increase rate is carried out by changing the rotational speed of the air pump 16 through the pump circuit 12, the pressure increase rate changing may be effected by regulating a flow control valve disposed in the piping 14 between the pump 16 and the cuff 10.

In the present embodiment, blood pressure measurement is carried out by detecting Korotkoff sounds during decrease of the cuff pressure. However, the monitor system may be adapted to measure blood pressure by detecting Korotkoff sounds when the cuff pressure is increased at a suitable rate after the cuff pressure has been increased to a predetermined low level at the first (low) or second (high) pressure increase rate.

Figure 3:
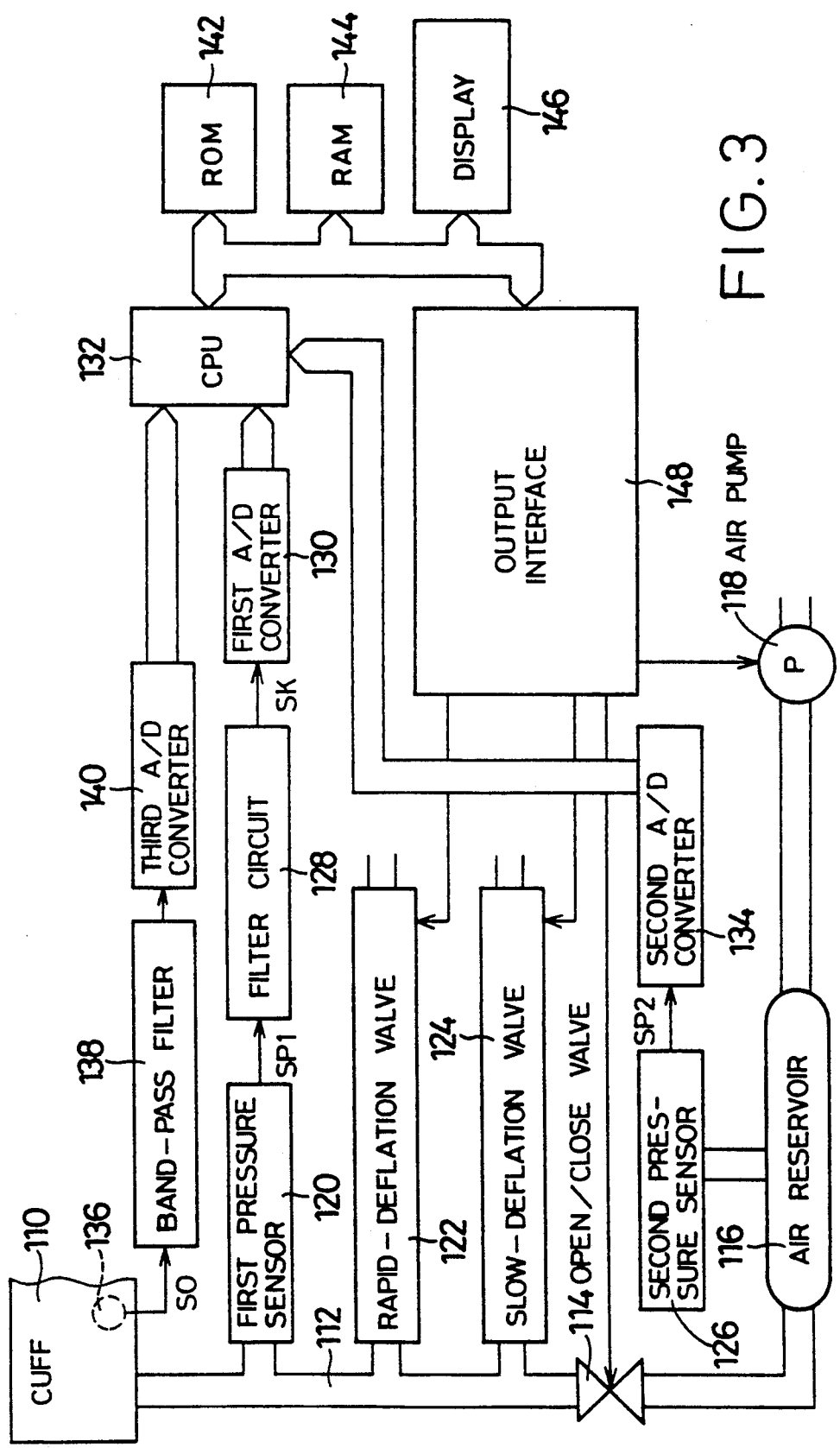
FIG. 3 is a diagrammatic view of a blood pressure measure system embodying the present invention.

Referring next to FIG. 3, there is shown the circuit diagram of a blood pressure measuring system embodying the present invention. Reference numeral 110 designates a rubber bag or cuff adapted to be wound around an upper arm or the like of a subject. An open/close valve 114, an air reservoir 116, and an air pump 118 are connected in series to the cuff 110 via piping 112. Compressed air is stored in the reservoir 116 by the pump 118. When the open/close valve 114 is opened, the compressed air is fed from the reservoir 116 to the cuff 110, so that the pressure in the cuff 110 (cuff pressure) is increased so as to press the upper arm of the subject. In the present embodiment, the cuff 110 serves as pressing means. Between the cuff 110 and the open/close valve 114, a first pressure sensor 120, a rapid-deflation valve 122, and a slow-deflation valve 124 are associated with the piping 112 in a parallel relationship with each other.

The first pressure sensor 120 detects the cuff pressure and generates a pressure signal $SP_1$ representing the detected cuff pressure, to a filter circuit 128. The filter circuit 128 includes a low-pass filter which transmits only a component representing a static pressure out of the cuff pressure (hereinafter, referred to as the "cuff pressure signal SK"). The cuff pressure signal SK is supplied to a central processing unit (CPU) 132 via a first analog to digital (A/D) converter 130. A second pressure sensor 126 is associated with the air reservoir 116. The second pressure sensor 126 detects the pressure in the air reservoir 116, and generates a pressure signal $SP_2$ representing the detected pressure, to the CPU 132 via a second A/D converter 134.

A microphone 136 is associated with the cuff 110. The microphone 136 detects arterial sounds (Korotkoff sounds) produced from an artery running in the upper arm of the subject, and generates a sound signal SO representing the detected Korotkoff sounds, to a band-pass filter 138. The band-pass filter 138 transmits only a component having a frequency of about 30 to 80 Hz. The sound signal SO transmitted through the band-pass filter 138 is supplied to the CPU 132 via a third A/D converter 140.

The CPU 132 is connected via data bus to a read only memory 142, a random access memory 144, a display 146, and an output interface 148. The CPU 132 processes input signals by utilizing control programs pre-stored in the ROM 142 and temporary-storage function of the RAM 144, and generates drive signals via the output interface 148 to drive circuits (not shown) for the open/close valve 114, air pump 118, and rapid- and slow-deflation valves 122, 124, so as to control the pump 118 and the valves 114, 122, 124, respectively. In addition, the CPU 132 operates for determining a blood pressure of the subject by utilizing the sound signal SO and cuff pressure signal SK, and commands the display 146 to indicate the determined blood pressure.

Figure 4:
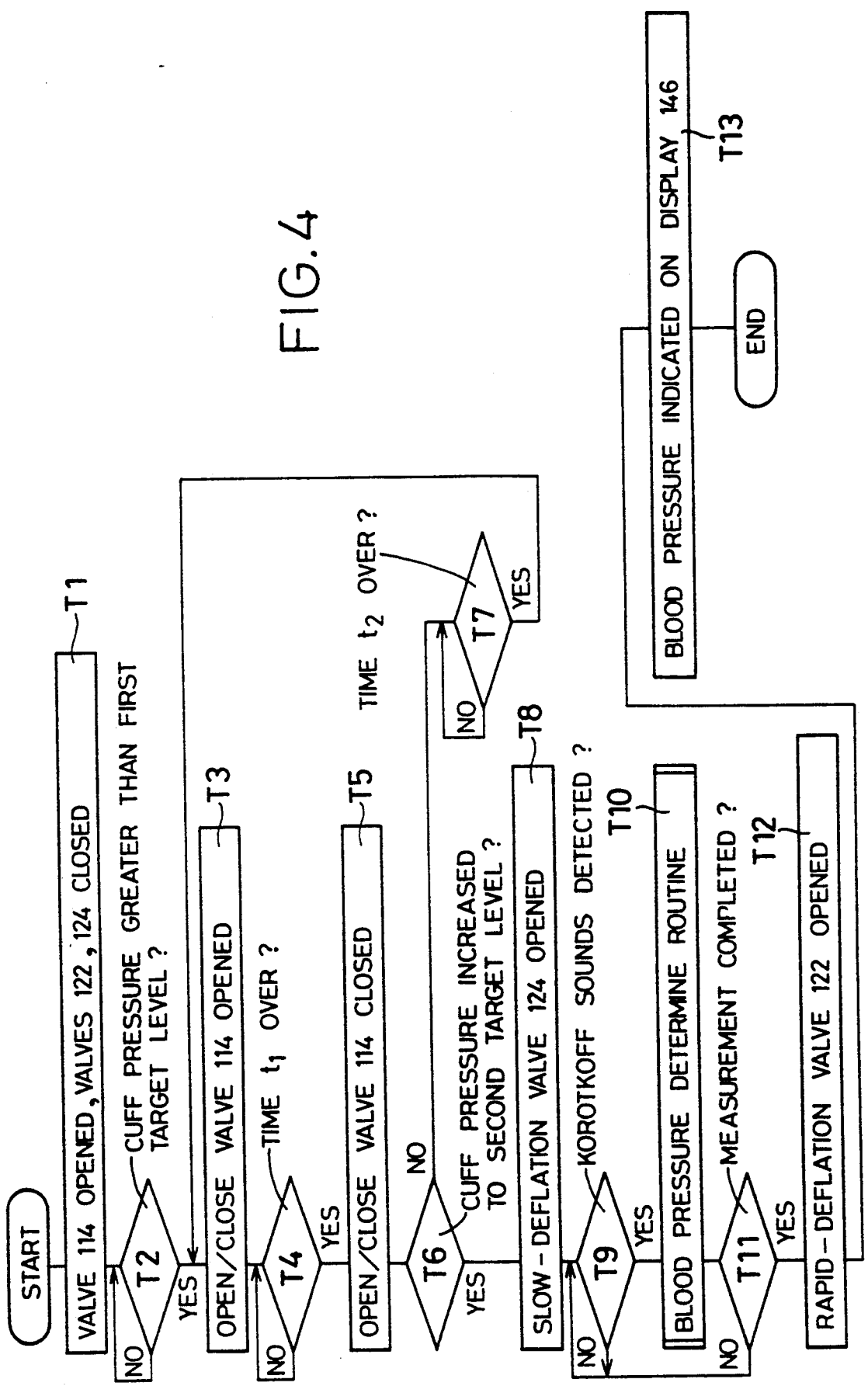
FIG. 4 is a flow chart for illustrating the operation of the measure system of FIG. 3.

By reference to the flow chart of FIG. 4, there will be described the operation of the blood pressure measure system constructed as described above.

When electric power is applied to the present system and a start switch (not shown) is turned ON, the control of the CPU 132 begins with Step T1 to open the open/close valve 114 and close the rapid- and slow-deflation valves 122, 124. After the electric power application, another program (not shown) is repetitively implemented by the CPU 132 for increasing the pressure in the air reservoir 116 to the upper limit of a predetermined pressure range and maintaining the air pressure within the predetermined range. This program is carried out by time sharing in a parallel relationship with the program indicated by the flow chart of FIG. 4.

Subsequently, the control of the CPU 132 goes to Step T2 to identify whether or not the cuff pressure has exceeded a first target pressure level such as 25 mmHg at which level the cuff 110 presses the upper arm of the subject with a low pressing force. If a negative judgement is made in Step T2, the control of the CPU 132 repeats Step T2. Meanwhile, if an affirmative judgement is made in Step T2, the control goes to Step T3 to open the open/close valve 114 and subsequently to Step T4 to identify whether or not a predetermined first period of time, $t_1$, (e.g., 0.3 second) has passed after the opening of the valve 114 in Step T3. If a negative judgement is made in Step ST4, the control of the CPU 132 repeats Step T4, so that the cuff pressure is increased by a suitable pressure while the valve 114 is kept open during the first period $t_1$.

Figure 5:
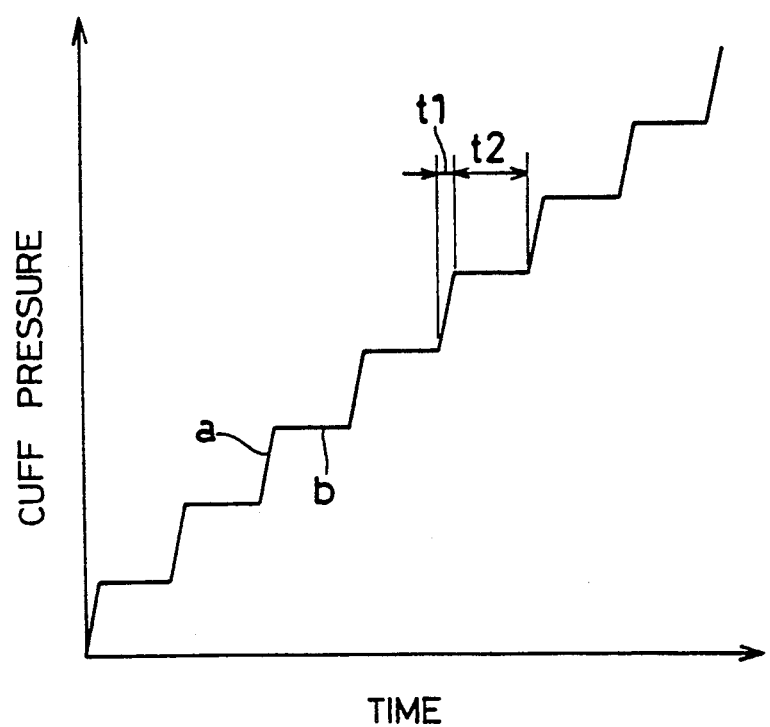
FIG. 5 is a graph of a stepped curve representing an automatic cuff pressure increase effected by the measure system of FIG. 3.

Meanwhile, if an affirmative judgement is made in Step T4, the control of the CPU 132 goes to Step T5 to close the open/close valve 114 and subsequently to Step T6 to identify whether or not the cuff pressure has exceeded a second target pressure level (e.g., 180 mmHg) which is estimated to be greater than the systolic blood pressure of the subject. If a negative judgement is made in Step T6, the control proceeds with Step T7 to identify whether or not a predetermined second period of time, $t_2$, (e.g., 0.7 second) has passed after the open/close valve 114 has been closed in Step T5. If a negative decision is made in Step T7, the control of the CPU 132 repeats Step S7, so that the open/close valve 114 is kept closed during the second period $t_2$ and accordingly the cuff pressure is prevented from being increased, namely, is maintained during the second period $t_2$. If the time $t_2$ has passed and an affirmative judgement is made in Step T7, the control of the CPU 132 goes back to Step T3 and the following steps. Thus, Steps T3 through T7 are repetitively implemented. Consequently, the cuff pressure is step-wise increased to the second target pressure level such as 180 mmHg, as indicated by a pressure-time curve shown in the graph of FIG. 5. The step-wise pressure increase includes the alternate first and second periods, a and b. The cuff pressure is increased in each of the first periods a and maintained in each of the second periods b.

If the cuff pressure has exceeded the second target pressure level and an affirmative judgement is made in Step T6, the control of the CPU 132 goes to Step T8 to open the slow-deflation valve 124. Thus, the cuff pressure starts to be decreased slowly. In the instant embodiment, the open/close valve 114, air cylinder 116, air pump 118, and Steps T3 through T7 cooperate with each other to serve as automatic regulating means for step-wise increasing the cuff pressure to a predetermined level. The first and second periods $t_1$, $t_2$ to open and close the open/close valve 114 and the air pressure at which to maintain the air reservoir 116 are pre-determined such that a curve representing the automatic cuff pressure increase effected by the present system is similar to a pressure increase curve representing a manual cuff inflation.

Step T8 is followed by Step T9 to identify whether or not a Korotkoff sound has been detected, by utilizing the sound signal SO. In the case where a negative judgement is made in Step T9, the control repeats Step T9. When an affirmative decision is made, a magnitude of the sound signal SO corresponding to the Korotkoff sound, and a magnitude of the cuff pressure signal SK at the time of detection of the Korotkoff sound, are stored in the RAM 144, in Step T9. Step T9 is followed by Step T10, namely, blood pressure determine routine.

In Step T10, a well-known blood pressure determine algorithm is implemented to determine, as systolic and diastolic blood pressures, the cuff pressures at the time of appearance and disappearance of the Korotkoff sounds, respectively. Step T10 is followed by Step T11 to identify whether or not the blood pressure measurement has been completed. If the measurement has not ended and therefore a negative judgement is made in Step T11, the control of the CPU 132 repeats Step T9 through Step T11. On the other hand, if the measurement has been completed and an affirmative judgement is made in Step T11, the control goes to Step T12 to open the rapid-deflation valve 122. Step T12 is followed by Step T13 to indicate the measured blood pressures on the display 146. Thus, a blood pressure measurement is ended. The present blood pressure measuring system may be adapted to periodically carry out blood pressure measurements at suitable intervals of time.

Conventional automatic cuff pressure increase is continuous, that is, has no pause. Therefore, a subject may feel uneasy as if he or she would continue to be pressed by the cuff endlessly, resulting in adversely affecting the accuracy of blood pressure measurement. In addition, wrinkles produced in the cuff surface during the automatic cuff pressure increase, may cause congestive spots in the subject's skin contacting the cuff surface, because the wrinkled cuff surface cannot naturally be recovered to the original smooth state due to the continuous pressure increase.

In contrast, in the instant embodiment, the automatic cuff pressure increase is effected such that a curve representing the automatic cuff pressure increase is similar to a stepped curve representing a manual cuff inflation. Therefore, a subject no longer feel as if he or she would be pressed endlessly. Thus, the present measure system advantageously reduces the uneasiness of the subject when the cuff pressure is automatically increased. In addition, the present measure system is free from adverse influence of such uneasiness to the accuracy of blood pressure measurement.

In the instant embodiment, wrinkles produced in the cuff surface during the cuff pressure increase, naturally are recovered to the original smooth surface during the second or pressure-maintaining periods b. Therefore, the present system does not suffer from the problem that congestive spots are produced in subject's skin under the the cuff because of the wrinkled cuff surface.

In addition, in the instant embodiment, the cuff pressure is increased without any pauses to the first target pressure level such as 25 mmHg corresponding to a low pressing force, and subsequently is step-wise increased to the second target pressure level such as 180 mmHg. This is advantageous in reducing the time necessary before commencement of the step-wise cuff pressure increase, namely, step-wise pressing force increase.

The present system is adapted such that the first and second periods $t_1$, $t_2$ to open and close the open/closed valve 114 and the air pressure at which to maintain the air reservoir 116 are pre-set at respective suitable values. However, it is possible to adapt the present system in such a way that those periods and pressure can manually be adjusted. In this case, the periods and pressure may be selected depending on, for example, estimated systolic blood pressure of a subject.

In the instant embodiment, the open/close valve 114 is opened and closed for respective suitable times $t_1$, $t_2$ under software control of the CPU 132, so that the cuff pressure is step-wise increased by pressurized air fed from the air reservoir 116. It is however possible to employ different manners of step-wise increasing the cuff pressure. For example, the open/close valve 114 may be controlled so that the actual cuff pressure represented by the signal SK from the first pressure sensor 120 coincides with or follows a pre-determined stepped pressure-time curve (i.e., function) which is pre-stored in the ROM 142. Furthermore, in the case where a high performance pump capable of increasing the cuff pressure at a sufficiently high rate is used as the air pump 118, the open/close valve 114 and air reservoir 116 may be omitted. Even in this case, the cuff pressure may be increased along a step-wise pressure increase curve, by on-off regulation of the air pump 118.

While, in the instant embodiment, the automatic cuff pressure increase is represented by a stepped curve similar to a manual cuff inflation curve, it is not required that the automatic cuff pressure increase curve be similar to a manual cuff pressure increase curve. Even in the case where cuff pressure is increased along a stepped curve which does not sufficiently approximate a manual cuff inflation curve, the above-described advantages with the instant embodiment are available to some extent.

Although, in both of the two embodiments of FIGS. 1 and 3, Korotkoff sounds are utilized for measuring blood pressure, it is possible to use different blood pressure measuring methods; for example, the "oscillometric" method wherein blood pressure is determined by utilizing magnitude variation of the pulse wave produced from an artery of a subject when the cuff pressure is varied.

While the present invention has been described in its presently preferred embodiments, it is to be understood that the present invention is not limited to the details of the illustrated embodiments but may be embodied with various changes, improvements and modifications that may occur to those skilled in the art without departing from the scope and spirit of the invention defined in the appended claims.

What is claimed is:

1. A blood pressure monitor system comprising:
    pressing means for applying a pressing force to a body portion of a subject;
    measuring means for increasing the pressing force of said pressing means to a predetermined level, subsequently varying said pressing force, and measuring a blood pressure of said subject during the variation of said pressing force, said measuring means repeating the blood pressure measurement;
    setting means for setting a frequency at which said measuring means repeats said blood pressure measurement; and
    changing means for changing a rate of increase of said pressing force depending upon the measurement frequency set by said setting means.

2. The monitor system according to claim 1, wherein said changing means is for judging whether or not said measurement frequency is greater than a reference value, and selecting a first pressing force increase rate if the judgement is negative and a second pressing force increase rate higher than said first increase rate if the judgement is affirmative.

3. The monitor system according to claim 2, wherein said pressing means comprises an inflatable cuff, said measuring means comprises an air pump which supplies said cuff with pressurized air, and said changing means comprises a pump drive/regular circuit which changes a rotational speed of said air pump in two steps depending upon the selected first or second increase rate.

4. The monitor system according to claim 1, wherein said setting means is manually operated to set a measurement period, thereby establishing said measurement frequency, said setting means providing to said changing means an electrical signal representing said measurement period.

5. The monitor system according to claim 4, further comprising means for measuring a time lapse from a time when said measuring means commences to increase said pressing force of said pressing means for carrying out said blood pressure measurement, so that, when the measured time lapse has exceeded said measurement period set by said setting means, said measuring means commences to increase said pressing force for a repeated blood pressure measurement.

6. A blood pressure measure system comprising:
    pressing means for applying a pressing force to a body portion of a subject, said pressing means comprising an inflatable cuff;
    automatic regulating means for step-wise increasing the pressing force of said pressing means to a predetermined target level, the step-wise increase of said pressing force including alternate first and second periods which are predetermined independently of detection of a bio-signal produced from said subject in synchronism with a heartbeat of said subject, said pressing force being increased in each of said first predetermined periods and maintained in each of said second predetermined periods,
    said regulating means comprising an open/close valve, an air reservoir, an air pump which supplies said reservoir with pressurized air, said open/close valve being opened during each said first period so as to allow the pressurized air in said reservoir to be supplied to the cuff and thereby increase a pressure in the cuff as the pressing force of said pressing means, said open/close valve being closed during each said second period so as to maintain the cuff pressure;
    means for increasing, in each said second period, a pressure in said reservoir with said pressurized air from said pump, to an upper limit of a predetermined pressure range, and subsequently maintaining the reservoir pressure within said pressure range; and
    measuring means for measuring a blood pressure of said subject while the cuff pressure as said pressing force is decreased after said step-wise increase.

7. The monitor system according to claim 6, wherein said pressing means comprises the inflatable cuff, and said regulating means step-wise increases said pressing force by step-wise increasing a pressure of said cuff to said predetermined target level higher than a systolic blood pressure of said subject.

8. The monitor system according to claim 7, wherein said regulating means step-wise increases said pressure of said cuff to said target level of 180 mmHg, which is normally higher than said systolic blood pressure of said subject.

9. The measure system according to claim 6, wherein said regulating means utilizes constant values as said first and second periods, respectively.

10. The measure system according to claim 6, wherein said regulating means increases said pressing force by a predetermined value in said each first period.

11. The measure system according to claim 6, wherein said measuring means periodically measures said blood pressure at predetermined intervals of time.

12. The measure system according to claim 6, wherein said regulating means effects said step-wise pressing force increase after having monotonously increased the pressing force to a predetermined low level.

13. The monitor system according to claim 12, wherein said pressing means comprises the inflatable cuff, and said regulating means begins said step-wise pressing force increase by step-wise increasing a pressure of said cuff at said predetermined low level lower than a diastolic blood pressure of said subject.

14. The monitor system according to claim 13, wherein said regulating means beings step-wise increasing said pressure of said cuff at said low level of 25 mmHg, which is normally lower than said diastolic blood pressure of said subject.

* * * * *